United States Patent
Kamachi et al.

(10) Patent No.: US 7,427,357 B2
(45) Date of Patent: Sep. 23, 2008

(54) PROCESS AND APPARATUS FOR ANAEROBIC TREATMENT OF SULFUR COMPOUND-CONTAINING WASTEWATER

(75) Inventors: Kazumasa Kamachi, Tokyo (JP); Yasuhiro Honma, Tokyo (JP); Toshihiro Tanaka, Tokyo (JP); Yuji Tsukamoto, Tokyo (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 10/564,483

(22) PCT Filed: Jul. 15, 2004

(86) PCT No.: PCT/JP2004/010424

§ 371 (c)(1),
(2), (4) Date: Mar. 14, 2007

(87) PCT Pub. No.: WO2005/007588

PCT Pub. Date: Jan. 27, 2005

(65) Prior Publication Data

US 2007/0175822 A1    Aug. 2, 2007

(30) Foreign Application Priority Data

Jul. 16, 2003   (JP) .............................. 2003-275308

(51) Int. Cl.
 *C02F 3/28* (2006.01)
 *C02F 1/20* (2006.01)
 *C02F 1/58* (2006.01)

(52) U.S. Cl. ........................ 210/603; 210/631; 210/916; 423/244.06

(58) Field of Classification Search ................. 210/603, 210/631, 916; 423/242.1, 244.01, 244.06
See application file for complete search history.

(56) References Cited

U.S. PATENT DOCUMENTS

5,916,438 A * 6/1999 Trocciola et al. ............. 210/188
2006/0243660 A1* 11/2006 Kamachi et al. ............. 210/603

FOREIGN PATENT DOCUMENTS

| DE | 226 552 | 8/1985 |
| JP | 57-136996 | 8/1982 |
| JP | 3-278892 | * 12/1991 |

(Continued)

*Primary Examiner*—Fred Prince
(74) *Attorney, Agent, or Firm*—Wenderoth, Lind & Ponack, L.L.P.

(57) ABSTRACT

An object of the present invention is to provide a process for a high-performance upflow anaerobic sludge treatment (methane fermentation treatment) targeting an organic wastewater containing an inorganic sulfur compound and an apparatus therefor. The invention relates to a process for methane fermentation treatment of an organic wastewater containing a sulfur compound, which includes: detecting a concentration of hydrogen sulfide in a biogas generated from a step of methane fermentation treatment; and, conducting a control of subjecting the organic wastewater to a desulfurization treatment operation in the case that the concentration of hydrogen sulfide in the biogas exceeds a predetermined value, and to an apparatus therefor. It is preferred that the predetermined value of the concentration of hydrogen sulfide is from 1 to 4%, preferably from 1% to 2%, and the desulfurization treatment operation comprises adding a desulfurizing agent containing an iron ion so that a molar ratio of the iron ion to sulfur is from 0.05 to 1.

2 Claims, 9 Drawing Sheets

FOREIGN PATENT DOCUMENTS

| | | |
|---|---|---|
| JP | 5-84499 | 4/1993 |
| JP | 6-47390 | 2/1994 |
| JP | 08-323387 | * 12/1996 |
| JP | 8-323387 | 12/1996 |
| JP | 10-305293 | * 11/1998 |
| JP | 2001-79590 | 3/2001 |

* cited by examiner

PROCESS AND APPARATUS FOR ANAEROBIC TREATMENT OF SULFUR COMPOUND-CONTAINING WASTEWATER

FIELD OF THE INVENTION

The present invention targets an organic wastewater containing an inorganic sulfur compound such as hydrogen sulfide, which is discharged from various factories such as paper-making factories and chemical factories, and the invention relates to a process for methane fermentation treatment for treating the wastewater and an apparatus therefor.

BACKGROUND ART

A process for methane fermentation treatment wherein an organic wastewater, an organic waste, or the like is treated by decomposition through methane fermentation is excellent in energy saving since energy for aeration is not required, excessive sludge is small, and energy can be recovered from a biogas generated as compared with aerobic treatment such as an active sludge process. However, since methane-producing bacteria or methane fermentation bacteria are low in growth rate and exhibit a bad precipitating ability, they are apt to flow out together with treated water. Therefore, it is difficult to increase microorganism density in a fermenter for use in methane fermentation treatment. Furthermore, there are problems in cost, building site, and the like.

As an anaerobic treatment process utilizing a highly efficient fermenter having a high microorganism density, there is an upflow anaerobic sludge blanket process (hereinafter referred to as "UASB"). It is a process recently widely used and has a characteristic that density of methane bacteria in a reactor can be maintained at a high density by granulation of anaerobic bacteria such as a methane bacterium in a granule form. As a result, an efficient treatment can be achieved even when the concentration of organic substances in the wastewater is considerably high.

However, in the conventional UASB process for a wastewater containing a high concentration of an inorganic sulfur compound such as hydrogen sulfide in a wastewater of chemical industries such as a wastewater of paper/pulp industries, since hydrogen sulfide in a raw water and hydrogen sulfide formed by sulfate reduction of sulfate ions inhibit methane fermentation, it is necessary to remove the same.

JP 5-84499 A discloses a methane fermentation treatment process wherein, in a medium-temperature methane fermentation of craft pulp wastewater by the upflow anaerobic sludge blanket process, sulfur matter in methanol-containing wastewater from a pulp cooking step was removed and then the wastewater was mixed with a wastewater containing polymeric hydrocarbons, followed by feeding the mixture to a methane fermentation reactor to treat it. However, there are problems that allowable sulfur matter is unclear and sulfur matter is excessively removed.

JP 2001-79590 A proposes a process of adding a hydrogen sulfide formation inhibitor to an organic wastewater containing a sulfate ion, in which hydrogen sulfide is generated, to form a sulfide and removing the formed sulfide through precipitation. In the process, a sulfide is formed by the action of a heavy metal contained in the hydrogen sulfide formation inhibitor and thereby hydrogen sulfide is precipitated and removed. In this process, however, there is a problem that methane fermentation is inhibited by the heavy metal contained therein.

Furthermore, JP 8-323387 A proposes a process for anaerobic treatment of an organic wastewater comprising adding an iron ion in an amount equimolar or more to the sulfur compound contained in the wastewater to the organic wastewater and conducting anaerobic treatment. In the process, there is a problem that iron is accumulated inside the methane fermenter since iron hydroxide flocks are formed from an iron ion excessively added relative to the sulfur compound.

DISCLOSURE OF THE INVENTION

However, there are the following problems in the conventional UASB process targeting a wastewater containing a high concentration of a sulfur compound such as hydrogen sulfide, e.g., the above wastewater of chemical industries such as a waster water of paper/pulp industries.

(a) Hydrogen sulfide is generated by reducing a sulfate ion and further, non-dissociative hydrogen sulfide is generated when pH is lowered. The non-dissociative hydrogen sulfide inhibits methane fermentation.

(b) Excessive removal of hydrogen sulfide by steam stripping or air stripping remarkably increases running cost.

(c) Excessive addition of a desulfurizing agent not only costs excessively but also damages anaerobic microorganisms considerably when excessive desulfurizing agent enters into the methane fermenter.

(d) When an iron ion as a hydrogen sulfide-removing agent is added excessively to the sulfur compounds, iron accumulates inside the reactor.

Accordingly, an object of the present invention is to provide a high-performance process for upflow anaerobic sludge blanket treatment targeting a wastewater containing an inorganic sulfur compound and an apparatus therefor.

The invention solves the above problems in the conventional art and provides a high-performance process for upflow anaerobic sludge blanket treatment targeting a wastewater containing a sulfur compound and an apparatus therefor.

As a result of the extensive studies for solving the above problems, the present inventors have found that methane fermentation is not inhibited by hydrogen sulfide when concentration of hydrogen sulfide in a biogas generated in methane fermentation treatment is less than 1%. Based on the finding, they have accomplished the invention.

Namely, the invention solves the above problems by the means described below.

(1) A process for methane fermentation treatment of an organic wastewater containing a sulfur compound, which comprises: detecting a concentration of hydrogen sulfide in a biogas generated from a step of methane fermentation treatment; and conducting a control of subjecting the organic wastewater to a desulfurization treatment operation in the case that the concentration of hydrogen sulfide in the biogas exceeds a predetermined value.

(2) The process for methane fermentation treatment of an organic wastewater according to item (1), wherein the predetermined value of the concentration of hydrogen sulfide is from 1% to 4%, preferably from 1% to 2%.

(3) The process for methane fermentation treatment of an organic wastewater according to item (1), wherein the desulfurization treatment operation is a desulfurization treatment of adding a desulfurizing agent containing an iron ion so that a molar ratio of the iron ion to sulfur is from 0.05 to 1.

(4) The process for methane fermentation treatment of an organic wastewater according to item (1), wherein the desulfurization treatment operation is a desulfurization treatment operation of adding a desulfurizing agent containing an insoluble iron.

(5) The process for methane fermentation treatment of an organic wastewater according to item (3) or (4), wherein the desulfurization treatment operation has a function of regenerating the desulfurizing agent by an aeration.

(6) An apparatus for methane fermentation treatment of an organic wastewater, which comprises: a desulfurization treatment tank or a liquid-transferring pipe where an organic wastewater containing a sulfur compound is subjected to a desulfurization treatment operation; and a methane fermenter where the organic wastewater subjected to the desulfurization treatment is subjected to methane fermentation treatment, wherein the methane fermenter has: a means for measuring a concentration of hydrogen sulfide in a gas generated in the fermenter; and a controlling means for controlling the desulfurization treatment based on the measured value.

(7) The apparatus for methane fermentation treatment of an organic wastewater according to item (6), wherein the desulfurization treatment tank has a function of regenerating the desulfurizing agent by an aeration.

According to the invention, in a process for methane fermentation treatment of an organic wastewater containing a sulfur compound, a stably high treatment efficiency is obtained by detecting concentration of hydrogen sulfide in a biogas generated from the methane fermentation treatment step and, in the case that the concentration of hydrogen sulfide in the biogas exceeds a predetermined value of 1% to 4%, preferably 1% to 2%, conducting control of subjecting the above organic wastewater to a desulfurization treatment operation.

In this connection, the reference numerals used in the drawings denote the followings, respectively.

1 raw water
2 raw water tank
3 raw water-transferring pipe
4 methane fermenter
5 baffle plate
6 gas-phase part
7 treated water pipe
8 treated water tank
9 generated gas-collecting pipe
10 gas analyzer for hydrogen sulfide
11 water-sealed tank
12 gas meter
13 gas holder
14 desulfurizing agent
15 apparatus for controlling feed of desulfurizing agent
16 nutrient source
17 treated water-circulating pipe

BEST MODE FOR CARRYING OUT THE INVENTION

The following will describe modes for carrying out the invention based on the drawings but the invention is not limited thereto.

As the methane fermentation treatment in the invention, there are high-load anaerobic treatment methods such as an upflow anaerobic sludge blanket process, a fluidized bed process, and a fixed bed process which subject a dissolved substance to anaerobic treatment and any methods can be adopted. Moreover, there may be employed a one-phase method wherein acid fermentation and methane fermentation are carried out in one reactor and a two-phase method wherein both reactions are carried out in separate reactors.

Figure 1:
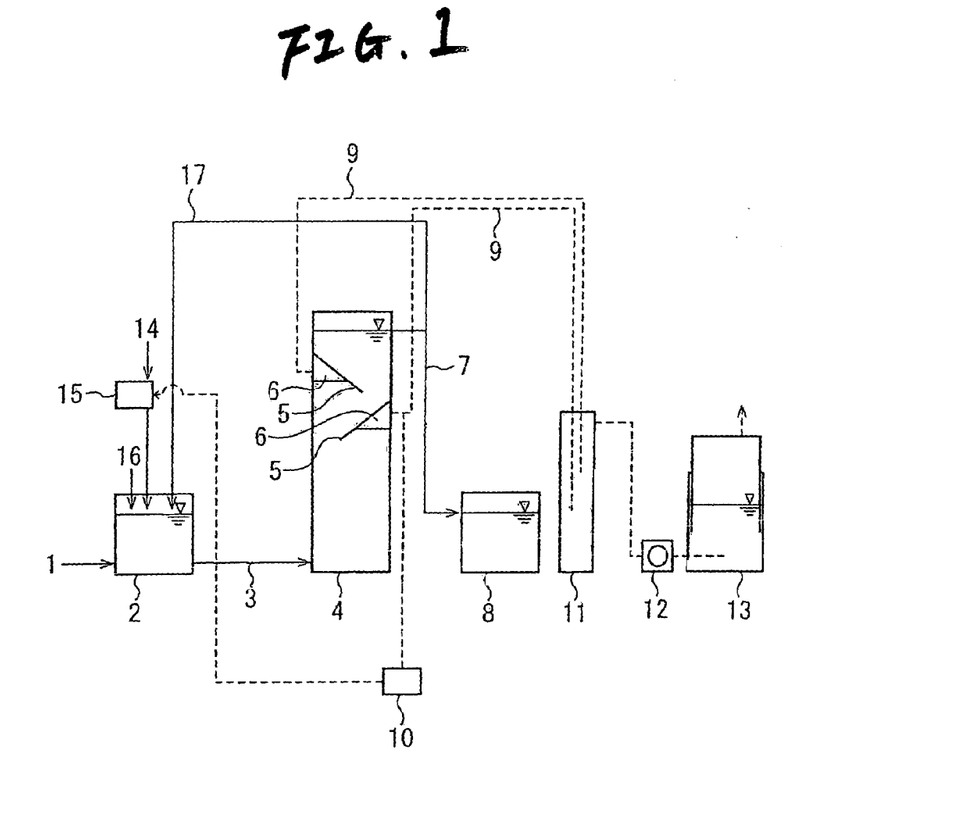
FIG. 1 is a system diagram of one embodiment of an upward flow anaerobic treatment apparatus of the invention.

FIG. 1 is a drawing illustrating an outline of one embodiment of a preferable upflow anaerobic treatment apparatus for conducting the process for methane fermentation treatment of the invention.

A raw water-transferring pipe 3 is connected and a cylindrical reactor whose upper and lower ends are closed (methane fermenter) 4 is provided. On both of right and left walls inside the reactor 4, baffle plates 5 are provided, one end of each plate being fixed and another end being extended in a descending manner toward an opposite side wall. The baffle plates 5 are provided at two places alternately side to side in the vertical direction. At a gas-phase part 6 where a generated gas gathers when the reaction starts, an exhaust of a generated gas-collecting pipe 9 which is connected to the outside is provided.

The exhaust of the generated gas-collecting pipe 9 connected with the gas-phase part 6 is opened in water in a water-sealed tank 11 filled with water. The opening position is a suitable depth of water at which water pressure is different and the water-sealed tank 11 is equipped with a gas meter 12 for measuring a gas flow discharged from the generated gas-collecting pipe 9. A gas holder 13 is provided at an end of the gas meter 12. Moreover, a treated water pipe 7 for discharging a supernatant liquid is opened at an upper end of the reactor 4. A gas analyzer for hydrogen sulfide 10 is provided between the gas-phase part 6 and the water-sealed tank 11.

The reactor 4 is used after granular sludge comprising anaerobic bacteria is charged. The anaerobic treatment as a target of the invention targets anaerobic treatment in a temperature range of medium-temperature methane fermentation treatment wherein optimal temperature ranges from 30° C. to 35° C. and high-temperature methane fermentation treatment wherein optimal temperature ranges from 50° C. to 55° C. Granular sludge comprising anaerobic bacteria is charged and a raw water (water to be treated) 1 is introduced from the liquid-transferring pipe 3 to the reactor 4. The raw water 1 is suitably diluted with a circulating liquid of treated water, water fed from the outside of the system, or the like, if necessary, and the flow rate of organic wastewater inside the reactor is controlled so as to be between 0.5 and 5m/h.

In a common methane fermentation, an acid fermenter (not shown in the figure) is provided in a precedent step of the methane fermenter 4. In the present treatment process, a desulfurization treatment operation may be conducted in a precedent step of the acid fermenter or a desulfurization treatment operation may be conducted between the acid fermenter and the methane fermenter 4. Since hydrogen sulfide is generated through the reduction of a sulfate ion in the acid fermenter, it is preferred to conduct the desulfurization treatment operation between the acid fermenter and the methane fermenter 4. Moreover, the desulfurization treatment operation of adding a desulfurizing agent 14 to the pipe 3 connected with the methane fermenter 4 can be also conducted.

Furthermore, by adding a nutrient source 16, e.g., minor metals such as Co and Ni to the raw water 1, it is possible to enhance activity of methane bacteria and improve a granule-forming ability.

Figure 2:
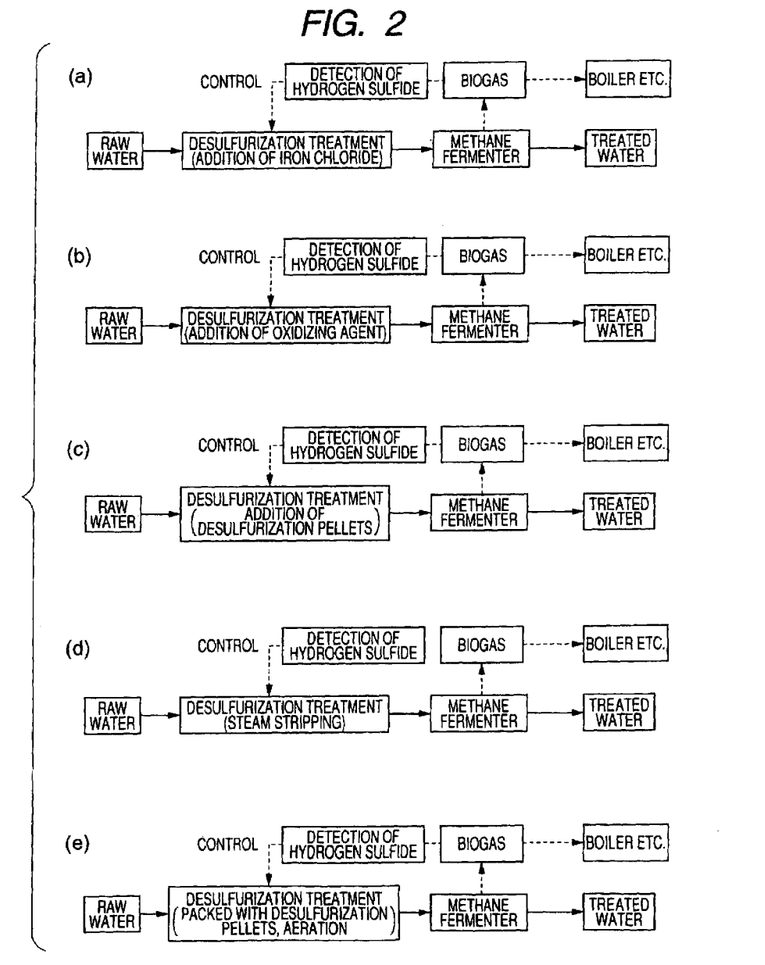
FIG. 2 is a block diagram exemplifying flows of respective Examples of the invention.

As the desulfurization treatment operation, flows shown in FIG. 2 may be mentioned as examples. The desulfurization treatment is carried out in a desulfurization treatment tank or a raw water-transferring pipe, but the other tank, e.g., a raw water tank may be used also as the desulfurization treatment tank without providing a dedicated tank. In the case that the desulfurization treatment is carried out with adding a desulfurizing agent, the treatment can be suitably carried out, for example, by adding the desulfurizing agent to the raw water tank as shown in FIG. 1.

In the case that the sulfur compound contained in the raw water 1 contains hydrogen sulfide as a main component, the water can be treated using steam stripping or gas stripping. In the case that a gas containing oxygen such as air is used in the gas stripping, it is necessary to introduce the raw water 1 into the methane fermenter 4 after dissolved oxygen concentration is lowered to a value at which anaerobic bacteria in the methane fermenter 4 are not inhibited.

The desulfurizing agent to be added may be any one as far as it is a desulfurizing agent which does not inhibit methane fermentation in a later step. Preferred are a desulfurizing agent containing an iron ion or a heavy metal such as $FeCl_3$ forming a hardly soluble sulfide with sulfur, a desulfurizing agent containing a heavy metal such as powdery or slurry iron oxide or iron hydroxide forming a hardly soluble sulfide with sulfur, a desulfurizing agent such as active carbon adsorbing a sulfur compound, and a desulfurizing agent comprising an oxidizing agent such as ozone, a chlorine-based oxidizing agent, or a bromine-based oxidizing agent oxidizing a reductive sulfur compound to sulfur.

An excessive amount of the oxidizing agent to be added not only costs excessively but also inhibits anaerobic bacteria in the later step. Particularly, in the case that an iron ion such as iron chloride is used as a desulfurizing agent, when the iron ion is added in an amount equimolar or less to sulfur, iron forms iron sulfide colloid, which is discharged to the outside of the system without accumulation at the inside of the methane fermenter 4. The addition of the iron ion in an amount equimolar or more to sulfur results in the formation of iron hydroxide flocks having a large precipitating ability owing to an excessive iron ion and accumulation thereof at the inside of the methane fermenter 4 occurs, so that the case is not preferred.

In the case that the concentration of sulfur compounds in the wastewater is stabilized, the desulfurization treatment operation may be conducted under constant conditions. However, when the concentration of sulfur compounds in wastewater fluctuates, it is necessary to control the desulfurization treatment operation. In the process of the invention, the desulfurization treatment operation can be controlled using the concentration of hydrogen sulfide in a biogas generated during methane fermentation treatment as an index. This is because the concentration of hydrogen sulfide in the gas varies depending on the concentration of hydrogen sulfide in the aqueous phase according to the desulfurization treatment operation. Moreover, measurement of the concentration of hydrogen sulfide in the biogas is easier than measurement of the concentration of hydrogen sulfide in water.

In order to determine an optimum desulfurization treatment operation, it is suitable to conduct the desulfurization treatment operation when the concentration of hydrogen sulfide detected by the above gas analyzer for hydrogen sulfide exceeds a predetermined value. The predetermined value is a concentration of hydrogen sulfide of 1% to 4%, preferably 1% to 2%. When the concentration of hydrogen sulfide in the generated gas is 1% or less, there is observed no inhibition of methane fermentation by the non-dissociative hydrogen sulfide.

Instead of using a heavy metal iron ion such as $FeCl_3$ forming a hardly soluble sulfide with sulfur, use can be made of insoluble iron such as an iron bar, steel wool, iron sand, scrap iron, pellets of a desulfurizing agent containing iron oxide, or iron hydroxide flocks. When desulfurization is carried out using the insoluble iron, most of iron sulfide formed attaches onto the surface of the desulfurizing agent and hence solid-liquid separation is easily achieved. Moreover, in the case of metallic iron, iron can be dissolved by electrification and thus the reaction of desulfurization can be controlled.

In the desulfurization treatment operation of adding a desulfurizing agent containing insoluble iron, when aeration is conducted by air blowing, iron sulfide is oxidized with oxygen to regenerate the desulfurizing agent, so that the amount of the agent to be charged can be reduced. The regeneration of the desulfurizing agent may be conducted simultaneously with the desulfurization treatment operation or may be conducted separately from the desulfurization treatment operation. Since the regeneration of the desulfurizing agent proceeds rapidly, the amount of aeration is considerably small as compared with the case of air stripping.

In the desulfurization treatment, the whole amount of the target raw water may be treated or part of the target raw water may be treated, and the desulfurization treated water may be mixed with the raw water.

EXAMPLES

The present invention is now illustrated in greater detail with reference to Examples, but it should be understood that the present invention is not to be construed as being limited thereto.

Examples 1 to 5 and Comparative Examples 1 and 2

(Treatment Process)

Example 1 is a process of adding $FeCl_3$ to a raw water as a desulfurization treatment operation in the case that concentration of hydrogen sulfide in a biogas exceeds 1.5%, Example 2 is a process of adding sodium hypochlorite as an oxidizing agent to a raw water as a desulfurization treatment operation in the case that concentration of hydrogen sulfide in a biogas exceeds 1.5%, Example 3 is a process of adding pellets of a desulfurizing agent comprising iron oxide to a raw water as a desulfurization treatment operation in the case that concentration of hydrogen sulfide in a biogas exceeds 1.5%, Example 4 is a process of subjecting a raw water to steam stripping as a desulfurization treatment operation in the case that concentration of hydrogen sulfide in a biogas exceeds 1.5%, and Example 5 is a process of aeration of a raw water tank packed with pellets of a desulfurizing agent as a desulfurization treatment operation in the case that concentration of hydrogen sulfide in a biogas exceeds 1.5%.

Comparative Example 1 is a process without any desulfurization treatment operation, and Comparative Example 2 is a process of adding a constant amount of $FeCl_3$ as a desulfurizing agent regardless of concentration of hydrogen sulfide in a biogas.

(Treatment Method)

The following sulfur-containing wastewater was treated in the apparatus of the invention shown in FIG. 1. In this connection, aeration in Example 5 was conducted with an air-diffusing pipe placed at the bottom part of the raw water tank.

In FIG. 2, (a) shows a flow in Example 1, (b) shows a flow in Example 2, (c) shows a flow in Example 3, (d) shows a flow in Example 4, and (e) shows a flow in Example 5.

In Examples 1 to 5 and Comparative Example 2, after a desulfurization treatment operation is conducted in the raw water tank which is a precedent step of the methane fermenter, the raw water was transferred to the methane fermenter. In Comparative Example 1, the raw water was transferred to the methane fermenter without adding any desulfurizing agent in the raw water tank.

(Experimental Conditions)

The volume of the methane fermenter is 3 m$^3$. The amount of a generated gas trapped at each baffle plate was measured by means of a gas meter placed at a water-sealed tank. The water temperature inside the methane fermenter was controlled so that it was maintained at 35° C.

As the raw water, use was made of water obtained by adding inorganic nutrient salts such as nitrogen and phosphorus and Ni and Co as minor elements to a wastewater containing methanol as a main component ($COD_{cr}$: 7,000 to 10,000 mg/L, dissolved sulfide: 100 to 600 mg/L).

By introducing part of treated water as a recycle liquid to the reactor together with the raw water, a water-introducing rate was set at 2 m/h. The ratio of the flow rate of the raw water to the amount of the recycled treated water was set according to COD load of the wastewater.

In the experiment, after running was carried out at a $COD_{cr}$ volume load of 25 kg/(m$^3$·d) stably for 100 days using a wastewater desulfurized by steam stripping beforehand, desulfurization treatment was carried out by the predetermined process in the case that concentration of hydrogen sulfide in a biogas exceeds 1.5%.

(Experimental Results)

Figure 3A:
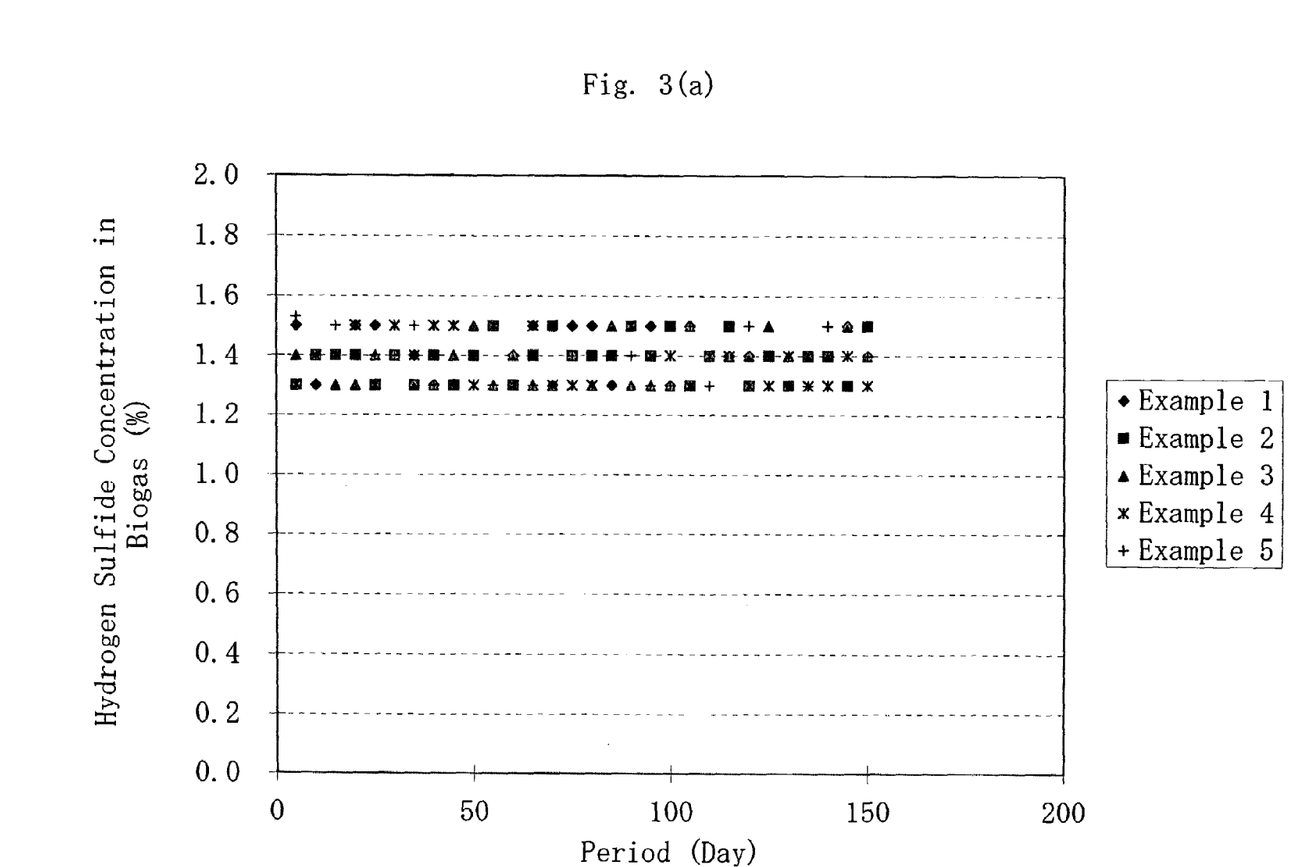
FIGS. 3(a) and 3(b) are dot graphs illustrating change with time of concentration of hydrogen sulfide in a biogas.
Figure 3B:
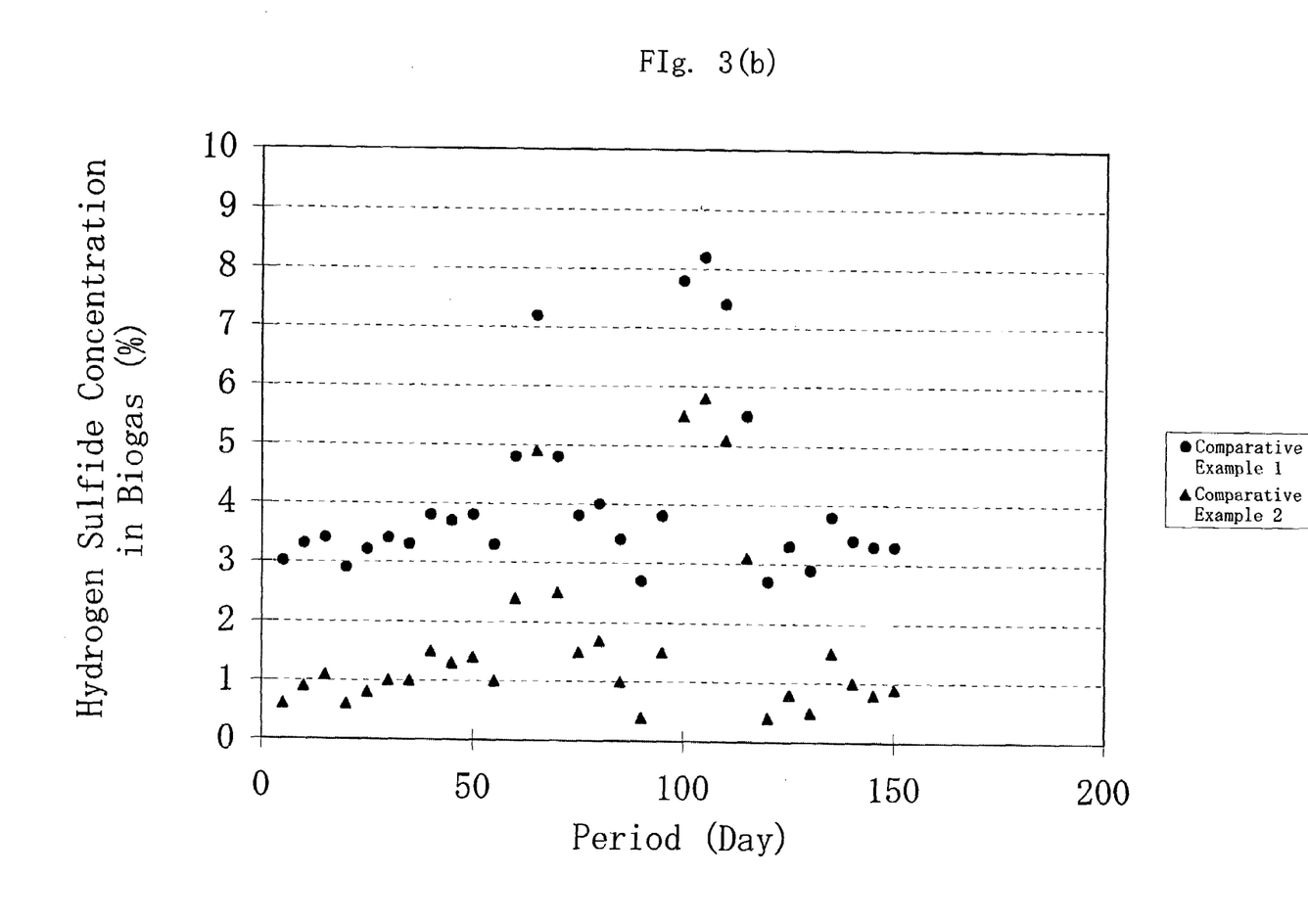
Figure 4A:
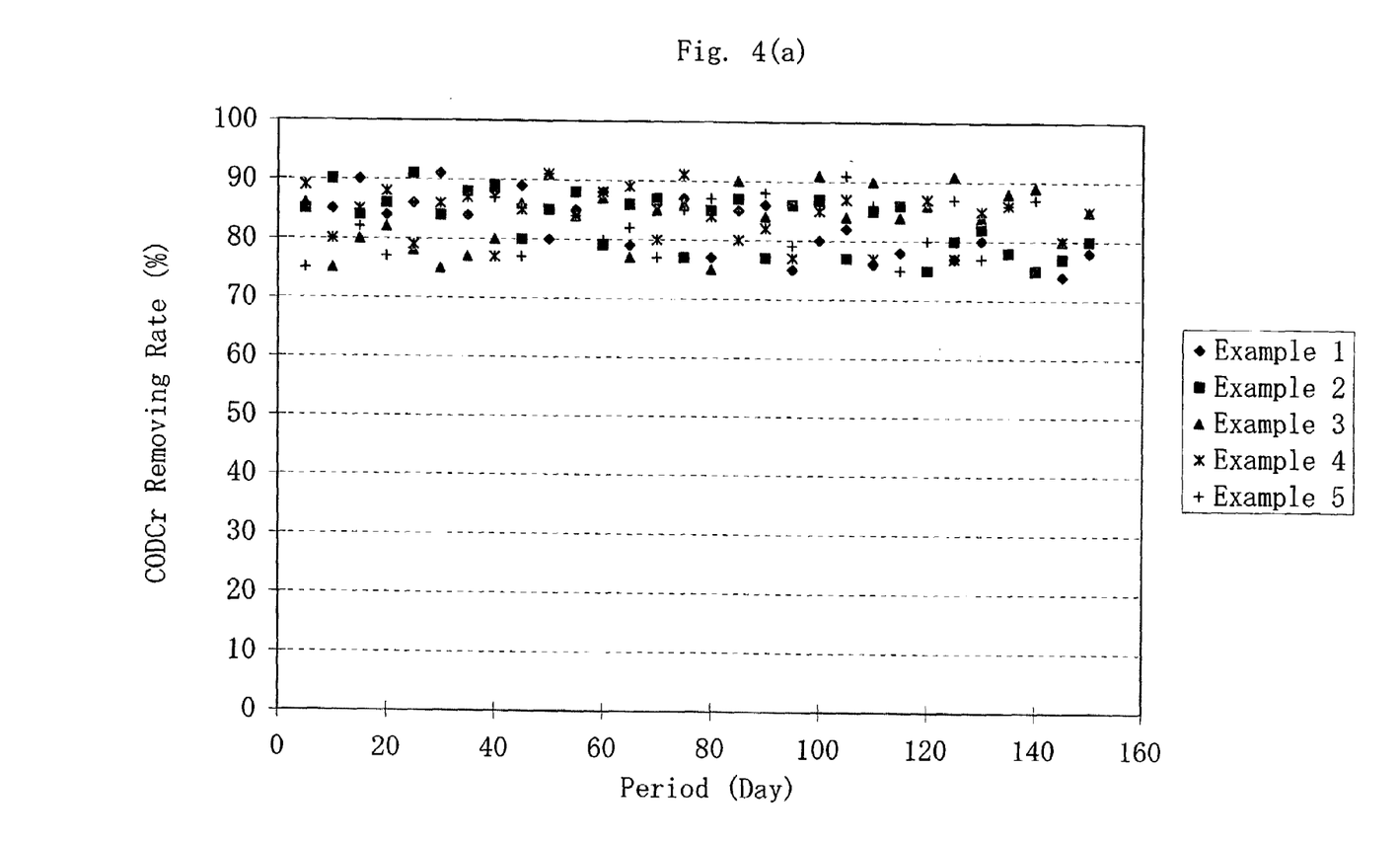
FIGS. 4(a) and 4(b) are dot graphs illustrating change with time in a COD removing rate.
Figure 4B:
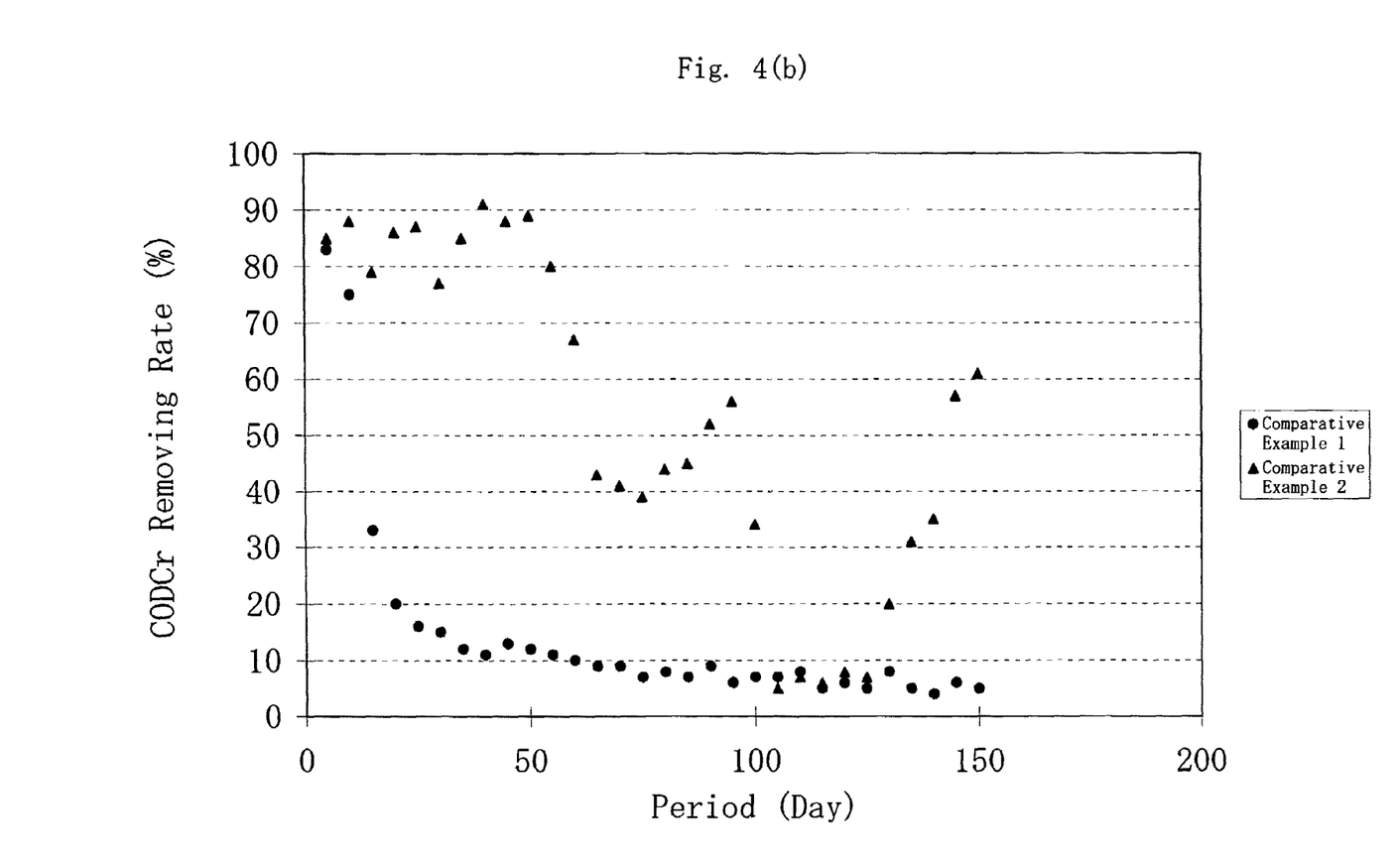
Figure 5A:
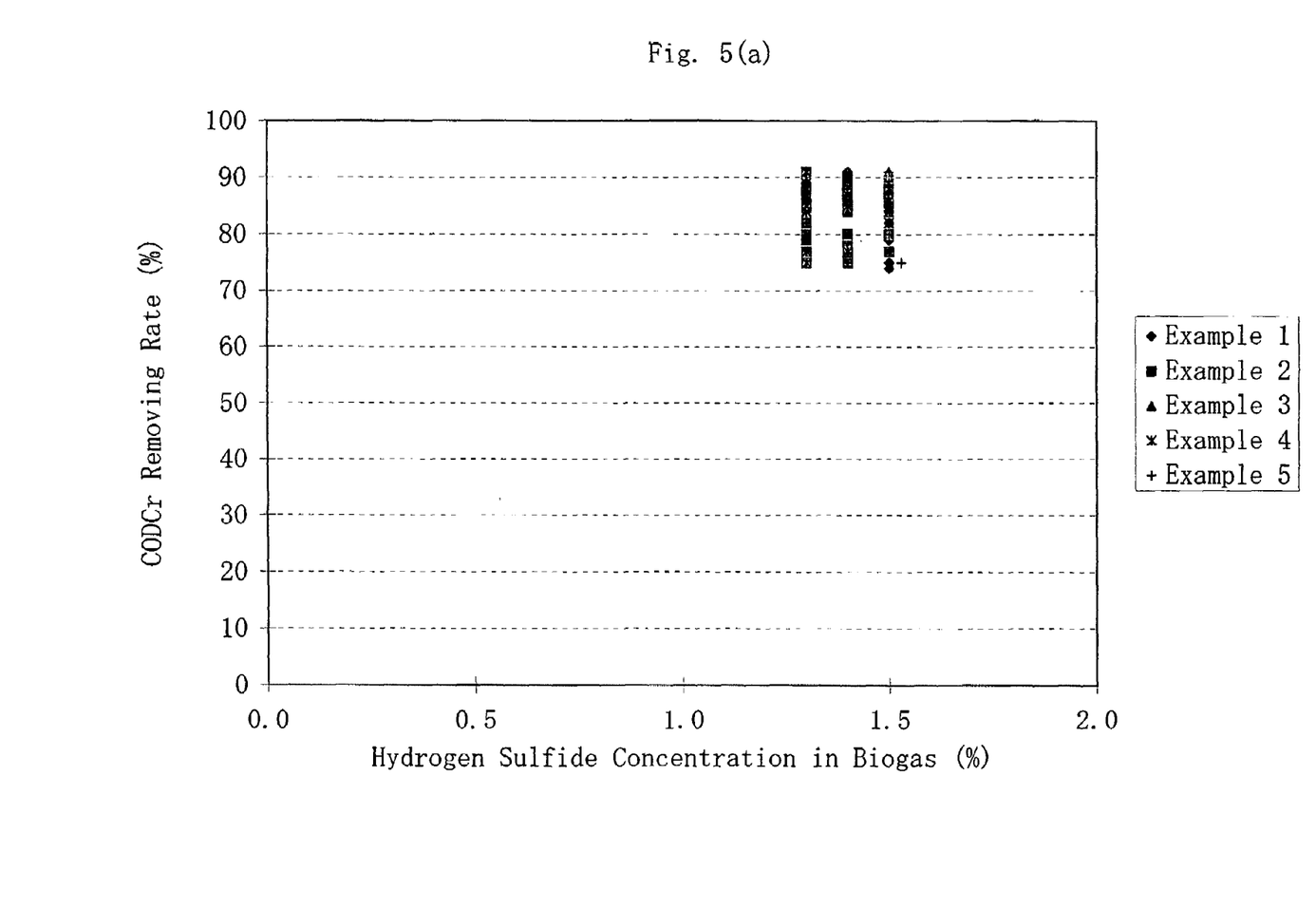
FIGS. 5(a) and 5(b) are dot graphs illustrating a relationship between concentration of hydrogen sulfide in a biogas and a COD removing rate in a biogas.
Figure 5B:
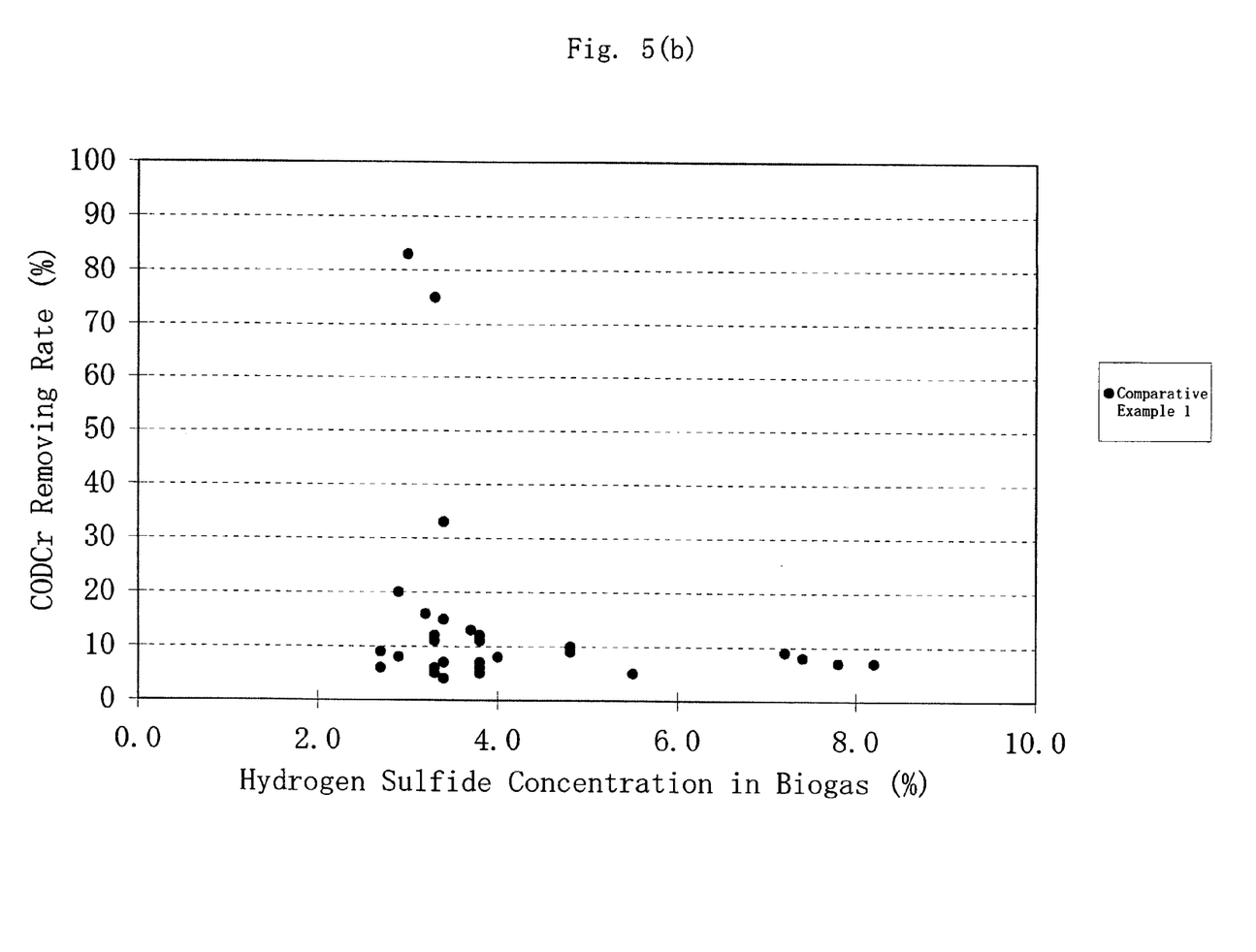

FIGS. 3(a) and 3(b) show concentration of hydrogen sulfide in a biogas in the methane fermenter, and FIGS. 4(a) and 4(b) show change in treatment results. FIGS. 5(a) and 5(b) show a relationship between concentration of hydrogen sulfide in the biogas and a $COD_{cr}$ removing rate. When the concentration of hydrogen sulfide in the biogas exceeds 3%, the $COD_{cr}$ removing rate remarkably decreased.

In Examples 1 to 5, a $COD_{cr}$ removing rate of about 80% was stably achieved in any case. On the other hand, the $COD_{cr}$ removing rate rapidly lowered in Comparative Example 1 and the $COD_{cr}$ removing rate decreased to 10% after 30 days. Moreover, the $COD_{cr}$ removing rate was unstable in Comparative Example 2. A high $COD_{cr}$ removing rate was obtained in the process of the invention.

In FIG. 3(a), it is revealed that the concentration of hydrogen sulfide in the biogas is 2% or less in every Example. Moreover, in FIG. 4(a) it is revealed that the $COD_{cr}$ removing rate is so high as 70% or more in every Example. FIG. 5(a) is an integration of FIG. 3(a) and FIG. 4(a) and the dots of respective Examples are gathered in an extremely narrow area. This fact clearly shows that the concentration of hydrogen sulfide in the biogas is 2% or less in every Example and thereby the $COD_{cr}$ removing rate reaches 70% or more.

Figure 6:
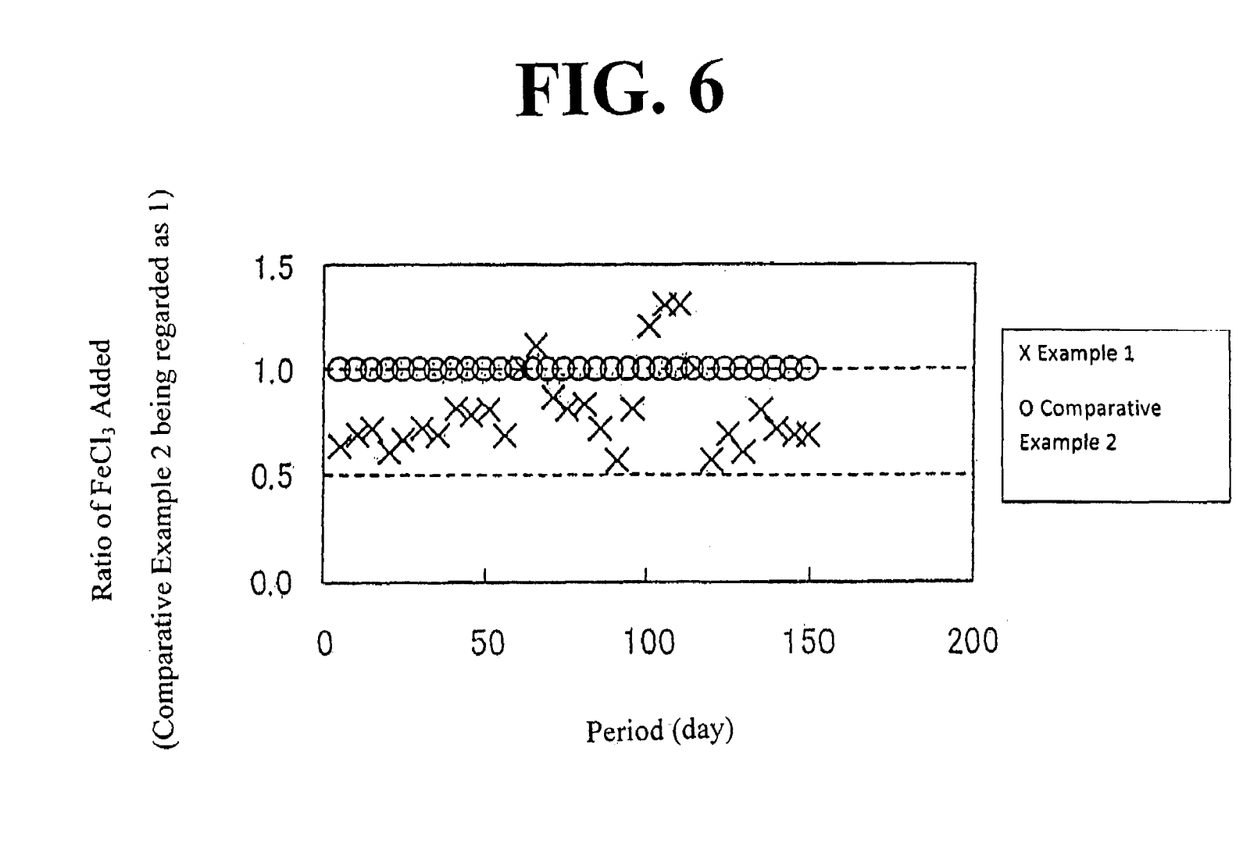
FIG. 6 is a dot graph illustrating change with time of added amount of $FeCl_3$ in Example 1 when the added amount of $FeCl_3$ in Comparative Example 2 is regarded as 1.

FIG. 6 is a dot graph illustrating change with time in the amount of $FeCl_3$ added in Example 1 when the amount of $FeCl_3$ added in Comparative Example 2 is regarded as 1. As compared with Comparative Example 2, the amount of $FeCl_3$ added can be reduced in Example 1.

While the present invention has been described in detail and with reference to specific embodiments thereof, it will be apparent to one skilled in the art that various changes and modifications can be made therein without departing from the spirit and scope thereof.

The present application is based on Japanese Patent Application No. 2003-275308 filed on Jul. 16, 2003, and the contents thereof are incorporated herein by reference.

INDUSTRIAL APPLICABILITY

According to the invention, inhibition of methane fermentation by non-dissociative hydrogen sulfide does not take place when an organic wastewater containing a sulfur compound, which is a raw water to be treated, is subjected to desulfurization treatment in the case that concentration of hydrogen sulfide in a biogas generated from a methane fermentation treatment step exceeds a predetermined value. When the anaerobic treatment process is employed, a high COD removing rate can be stably achieved, so that it becomes possible to conduct an effective anaerobic treatment of an organic industrial wastewater containing inorganic sulfur compounds such as hydrogen sulfide discharged from various factories such as paper-making factories and chemical factories.

What is claimed is:

1. A process for methane fermentation treatment of an organic wastewater containing a sulfur compound using an upflow anaerobic sludge blanket treatment apparatus, comprising:

feeding organic wastewater to said upflow anaerobic sludge blanket treatment apparatus, so a flow rate of said organic wastewater inside said apparatus is between 0.5 and 5 m/h;

detecting a concentration of hydrogen sulfide in a biogas generated in said apparatus; and subjecting said organic wastewater which flows into said apparatus to a desulflirization treatment operation when the concentration of hydrogen sulfide in the biogas exceeds a predetermined value between 1 and 2%, wherein the desulfurization treatment is a desulfurization treatment by adding a desulfurization agent containing an iron ion.

2. The process for methane fermentation treatment of an organic wastewater according to claim 1, wherein the desulfurizing agent is added so that a molar ratio of the iron ion to sulfur compound is between 0.05 and 1.

* * * * *